United States Patent
Amirim

(10) Patent No.: US 9,241,650 B2
(45) Date of Patent: Jan. 26, 2016

(54) PATIENT SPECIFIC QRS COMPLEX CLASSIFICATION FOR ARRHYTHMIA DETECTION

(71) Applicant: LifeWatch Technologies Ltd., Rehovot (IL)

(72) Inventor: Mordehay Amirim, Rehovot (IL)

(73) Assignee: LIFEWATCH TECHNOLOGIES LTD., Rehovot (IL)

( * ) Notice: Subject to any disclaimer, the term of this patent is extended or adjusted under 35 U.S.C. 154(b) by 94 days.

(21) Appl. No.: 14/106,772

(22) Filed: Dec. 15, 2013

(65) Prior Publication Data

US 2015/0164359 A1    Jun. 18, 2015

(51) Int. Cl.
*A61B 5/0472* (2006.01)
*G06K 9/00* (2006.01)
*A61B 5/0452* (2006.01)
*A61B 5/00* (2006.01)

(52) U.S. Cl.
CPC ............. *A61B 5/0472* (2013.01); *A61B 5/7264* (2013.01); *G06K 9/00496* (2013.01); *A61B 5/04525* (2013.01); *A61B 5/746* (2013.01)

(58) Field of Classification Search
CPC .. A61B 5/0472; A61B 5/0452; A61B 5/0464; A61B 5/046; A61B 5/0456; A61B 5/04525; A61B 5/0468
USPC .......................................... 600/515, 516, 517
See application file for complete search history.

(56) References Cited

U.S. PATENT DOCUMENTS 5,819,007 A * 10/1998 Elghazzawi ..................... 706/46
5,908,393 A * 6/1999 Albrecht et al. .............. 600/509

* cited by examiner

*Primary Examiner* — Amanda Patton
*Assistant Examiner* — Philip Edwards
(74) *Attorney, Agent, or Firm* — Reches Patents

(57) ABSTRACT

A method for QRS classification, the method may include generating, by a computer and based upon information representative of multiple QRS complexes of a patient, a QRS complex cluster tree; and updating, by the computer, the QRS complex cluster tree based upon information relating to other QRS complexes of the patient.

26 Claims, 11 Drawing Sheets

PATIENT SPECIFIC QRS COMPLEX CLASSIFICATION FOR ARRHYTHMIA DETECTION

FIELD OF THE INVENTION

The invention relates to analysis of QRS complex data in either real time or batch systems.

BACKGROUND OF THE INVENTION

QRS complex is a waveform presented in an electrocardiograph device during ventricular depolarization.

Various heart disorders can be detected by analyzing QRS complexes and the timing differences between consecutive QRS complexes.

There is a growing need to provide efficient systems and methods for QRS complex analysis.

SUMMARY OF THE INVENTION

According to various embodiments of the invention there may provided a method for QRS classification, the method may include generating, by a computer and based upon information representative of multiple QRS complexes of a patient, a QRS complex cluster tree; and updating, by the computer, the QRS complex cluster tree based upon information relating to other QRS complexes of the patient.

The generating of the QRS complex cluster tree may include calculating QRS complex clusters; and associating different QRS complex clusters to different leaves of the QRS complex cluster tree.

The calculating of the QRS complex clusters may be based solely on the information representative of the multiple QRS complexes of the patient.

The method may include labeling the QRS complex clusters based upon (a) the information representative of the multiple QRS complexes of the patient, and (b) information representative of QRS complexes of at least one other person.

The calculating of the QRS complex clusters may include calculating, for each QRS complex cluster, a QRS complex template based upon the information representative of multiple QRS complexes of a patient; and clustering based upon statistical attributes to the QRS complex template.

The QRS complex template of a QRS complex cluster may be a weighted mean of QRS complex vectors that belong to the QRS complex cluster.

The QRS complex template of a QRS complex cluster may be a median of QRS complex vectors that belong to the QRS complex cluster.

The updating of the QRS complex cluster tree may include receiving another QRS complex of the patient; classifying the other QRS complex thereby finding a best matching cluster; and responding to the finding of the best matching cluster.

The responding may include sending an alert about a medical event of which the other QRS complex may be indicative of.

The information representative of multiple QRS complexes of a patient may be obtained from a single lead.

The information representative of multiple QRS complexes of a patient may be obtained from multiple leads.

According to various embodiments of the invention there may provided a non-transitory computer readable medium may store instructions that once executed by the computer cause the computer to execute the stage of generating, based upon information representative of multiple QRS complexes of a patient, a QRS complex cluster tree; and updating the QRS complex cluster tree based upon further information relating to other QRS complexes of the patient.

The non-transitory computer readable medium may store instructions for generating of the QRS complex cluster tree by calculating QRS complex clusters; and associating different QRS complex clusters to different leaves of the QRS complex cluster tree.

The non-transitory computer readable medium may store instructions for calculating of the QRS complex clusters based solely on the information representative of the multiple QRS complexes of the patient.

The non-transitory computer readable medium may store instructions for labeling the QRS complex clusters based upon (a) the information representative of the multiple QRS complexes of the patient, and (b) information representative of QRS complexes of at least one other person.

The non-transitory computer readable medium may store instructions for calculating of the QRS complex clusters by calculating, for each QRS complex cluster, a QRS complex template based upon the information representative of multiple QRS complexes of a patient; and clustering based upon statistical attributes of the QRS complex template.

The QRS complex template of a QRS complex cluster may be a weighted mean of QRS complex vectors that belong to the QRS complex cluster.

The QRS complex template of a QRS complex cluster may be a median of QRS complex vectors that belong to the QRS complex cluster.

The non-transitory computer readable medium may store instructions for updating of the QRS complex cluster tree by receiving another QRS complex of the patient; classifying the other QRS complex thereby finding a best matching cluster; and responding to the finding of the best matching cluster.

The non-transitory computer readable medium may store instructions for responding by sending an alert about a medical event of which the other QRS complex may be indicative of.

The information representative of multiple QRS complexes of a patient may be obtained from a single lead.

The information representative of multiple QRS complexes of a patient may be obtained from multiple leads.

According to various embodiments of the invention there may provided a system for QRS classification, the system may include a computer that may include a QRS classifier that it arranged to generate, based upon information representative of multiple QRS complexes of a patient, a QRS complex cluster tree; and update the QRS complex cluster tree based upon further information relating to other QRS complexes of the patient.

The QRS classifier may be arranged to calculate QRS complex clusters; and associate different QRS complex clusters to different leaves of the QRS complex cluster tree.

The QRS classifier may be arranged to calculate the QRS complex clusters solely on the information representative of the multiple QRS complexes of the patient.

The QRS classifier may be arranged to calculate a QRS complex template of a QRS complex cluster as a weighted mean of QRS complex vectors that belong to the QRS complex cluster.

The QRS classifier may be arranged to calculate a QRS complex template of a QRS complex cluster as a median of QRS complex vectors that belong to the QRS complex cluster.

The QRS classifier may be arranged to calculate a template QRS complex vector of the based upon the information representative of multiple QRS complexes of a patient; and cluster based upon statistical attributes to the template QRS complex.

The QRS classifier may be arranged to receive another QRS complex of the patient out of the other QRS complexes of the patient; classify the QRS complex thereby finding a best matching cluster; and wherein the system may include an event detector that may be arranged to respond to the finding of the best matching cluster.

The event detector may be arranged to send an alert about a medical event of which the other QRS complex may be indicative of.

The information representative of multiple QRS complexes of a patient may be obtained from a single lead.

The information representative of multiple QRS complexes of a patient may be obtained from multiple leads.

BRIEF DESCRIPTION OF THE DRAWINGS

The foregoing and other objects, features, and advantages of the present invention will become more apparent from the following detailed description when taken in conjunction with the accompanying drawings. In the drawings, similar reference characters denote similar elements throughout the different views, in which.

DETAILED DESCRIPTION OF THE DRAWINGS

Figure 1:
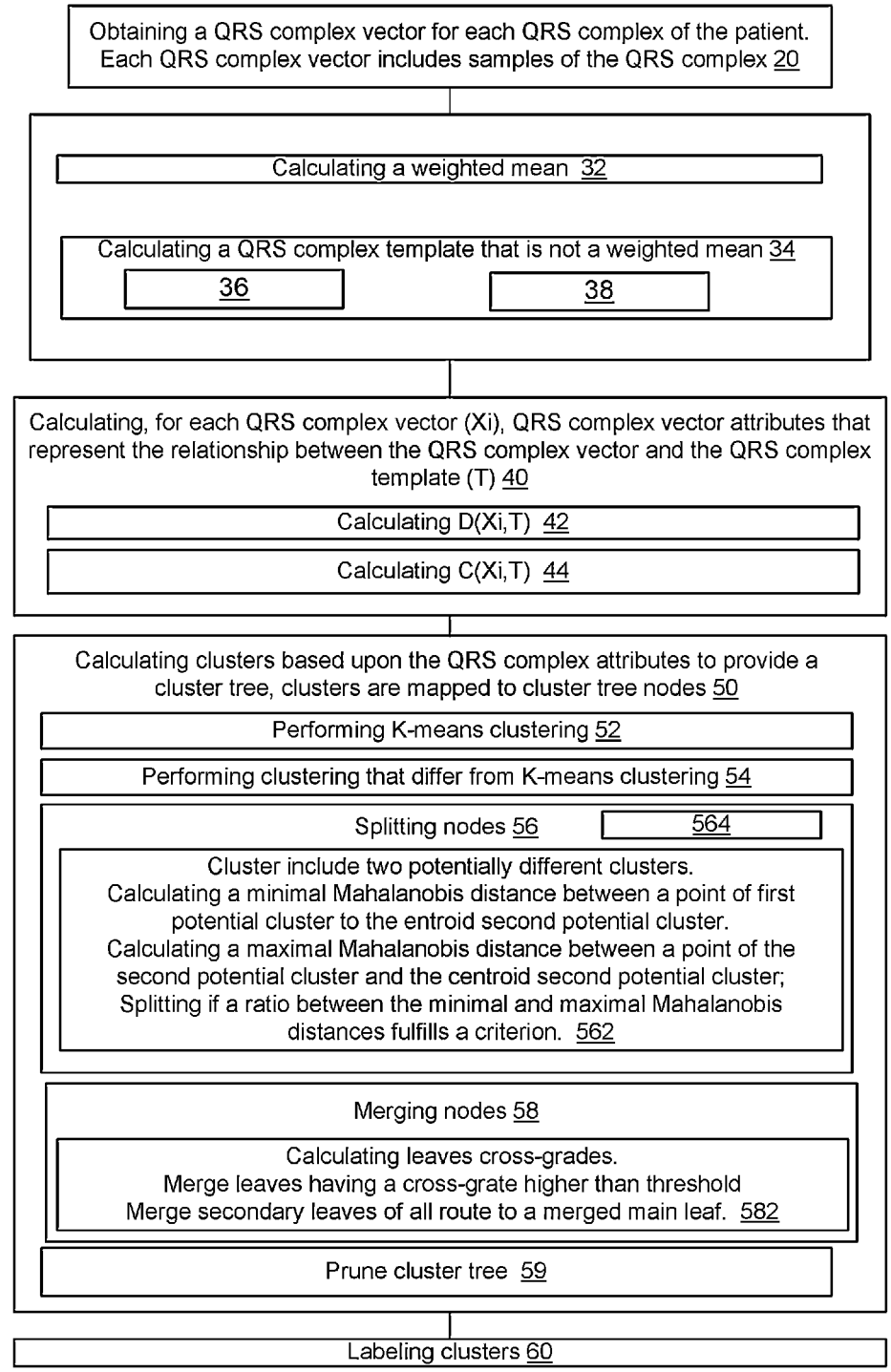
FIG. 1 illustrates a method according to an embodiment of the invention.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

Because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

Any reference in the specification to a method should be applied mutatis mutandis to a system capable of executing the method and should be applied mutatis mutandis to a non-transitory computer readable medium that stores instructions that once executed by a computer result in the execution of the method.

Any reference in the specification to a system should be applied mutatis mutandis to a method that may be executed by the system and should be applied mutatis mutandis to a non-transitory computer readable medium that stores instructions that may be executed by the system.

Any reference in the specification to a non-transitory computer readable medium should be applied mutatis mutandis to a system capable of executing the instructions stored in the non-transitory computer readable medium and should be applied mutatis mutandis to method that may be executed by a computer that reads the instructions stored in the non-transitory computer readable medium.

The following explanation may refer to a cluster tree that is binary. It will be appreciated that the binary tree is merely a non-limiting example and that the cluster tree can be a non-binary cluster tree.

The following explanation may refer to a QRS complex vector. It will be appreciated that a QRS complex can be represented in other manner and that the vector representation (QRS complex vector) is merely a non-limiting example.

The terms "cluster" and "node" are used in an interchangeable manner. A cluster is represented by a leaf node of the cluster tree.

There is provided a classifier that is designed to have a dynamic cluster tree (such a dynamic binary tree) which holds all the patient QRS complexes statistics learned by the algorithm on real-time. The classifier may calculate different QRS complex templates (representative of clusters) and then classify incoming QRS complex vectors according to the clusters.

The classifier may use adaptive patient based features, which are calculated relatively to the patient QRS complexes templates.

Figure 2:
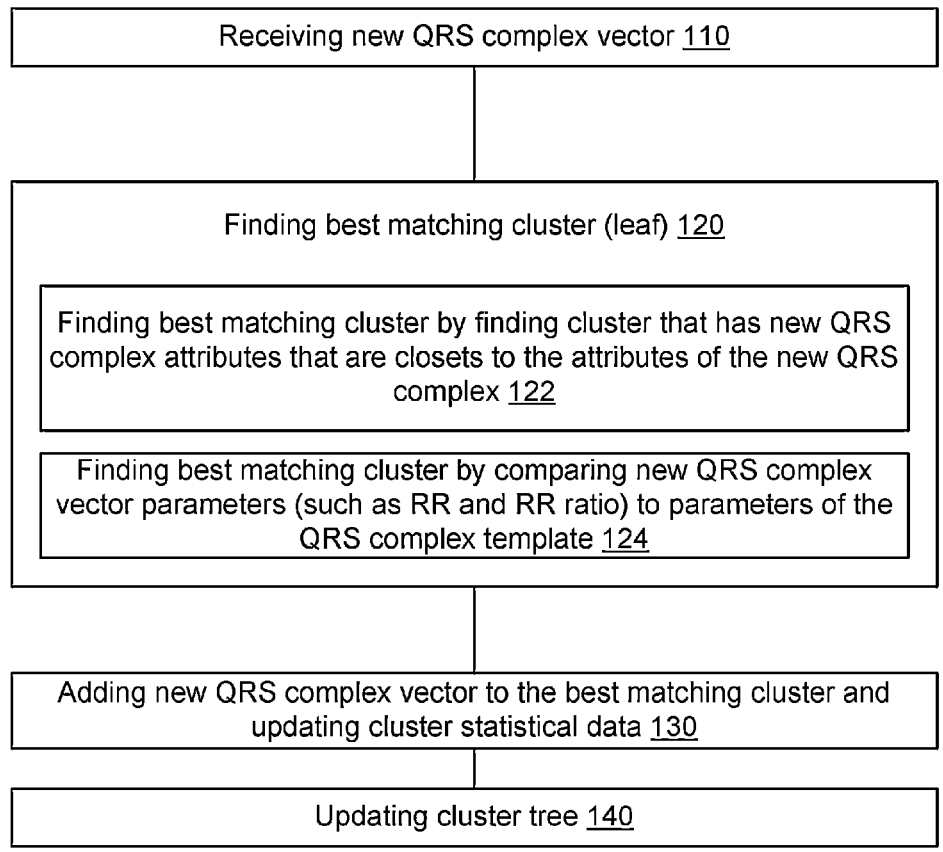
FIG. 2 illustrates a method according to an embodiment of the invention.

The algorithm includes an initialization phase (FIG. 1) and an update phase (FIG. 2).

Initialization Phase

During the initialization phase the algorithm builds a representative cluster tree from an initial set of training set of QRS complexes. All the QRS complexes form clusters that are represented by the leaves of the cluster tree.

Figure 3:
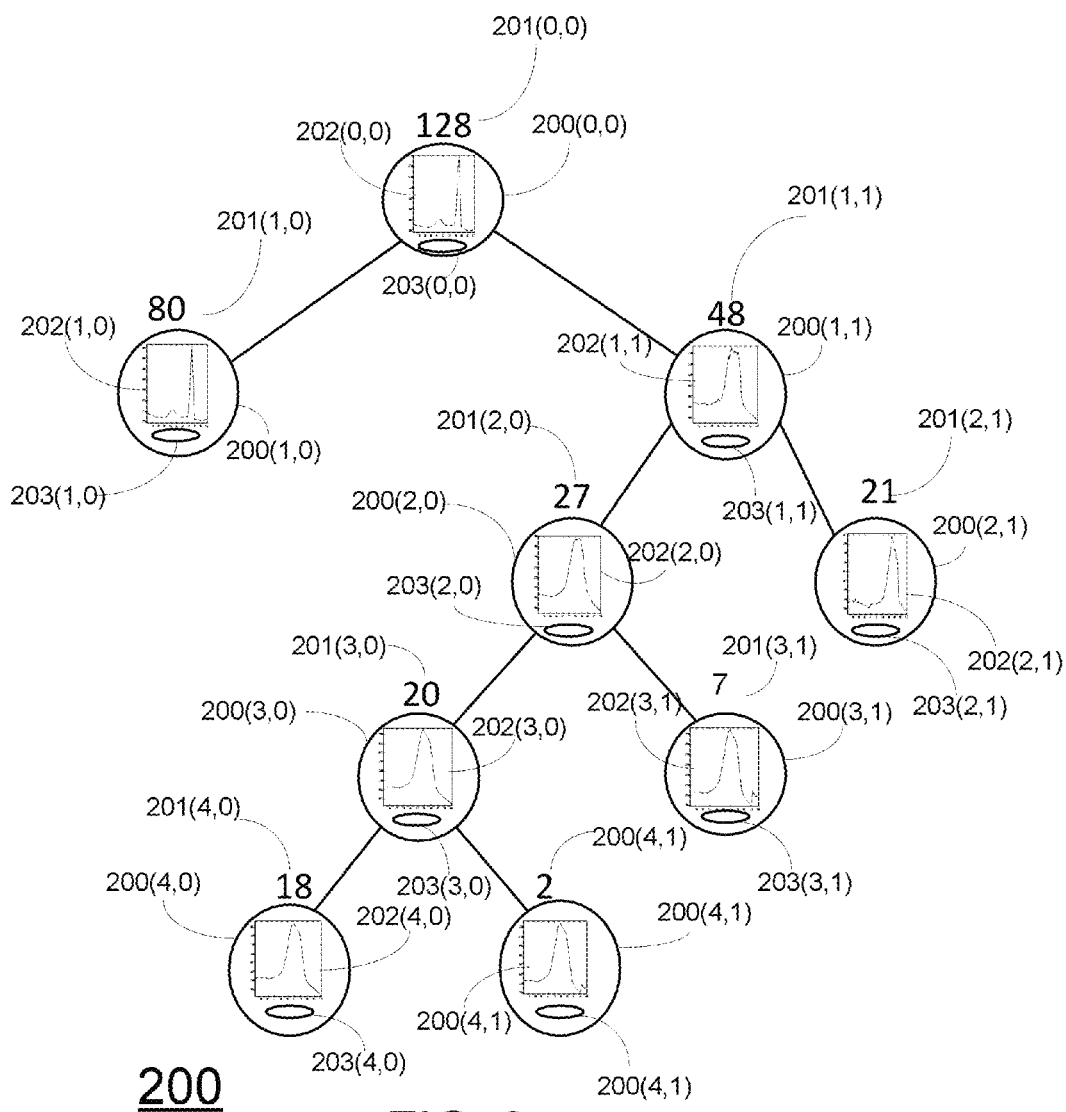
FIG. 3 illustrates a cluster tree according to an embodiment of the invention.
Figure 4:
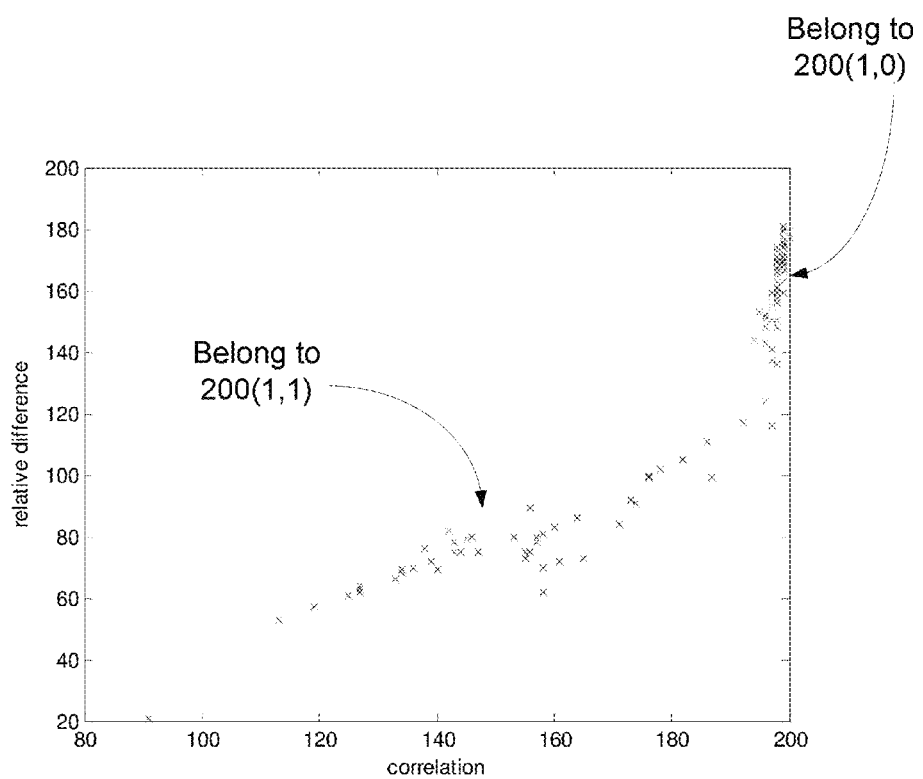
FIG. 4 illustrates attributes of QRS complex vectors that belong to a node of the cluster tree that is about to be split to two nodes according to an embodiment of the invention.
Figure 5:
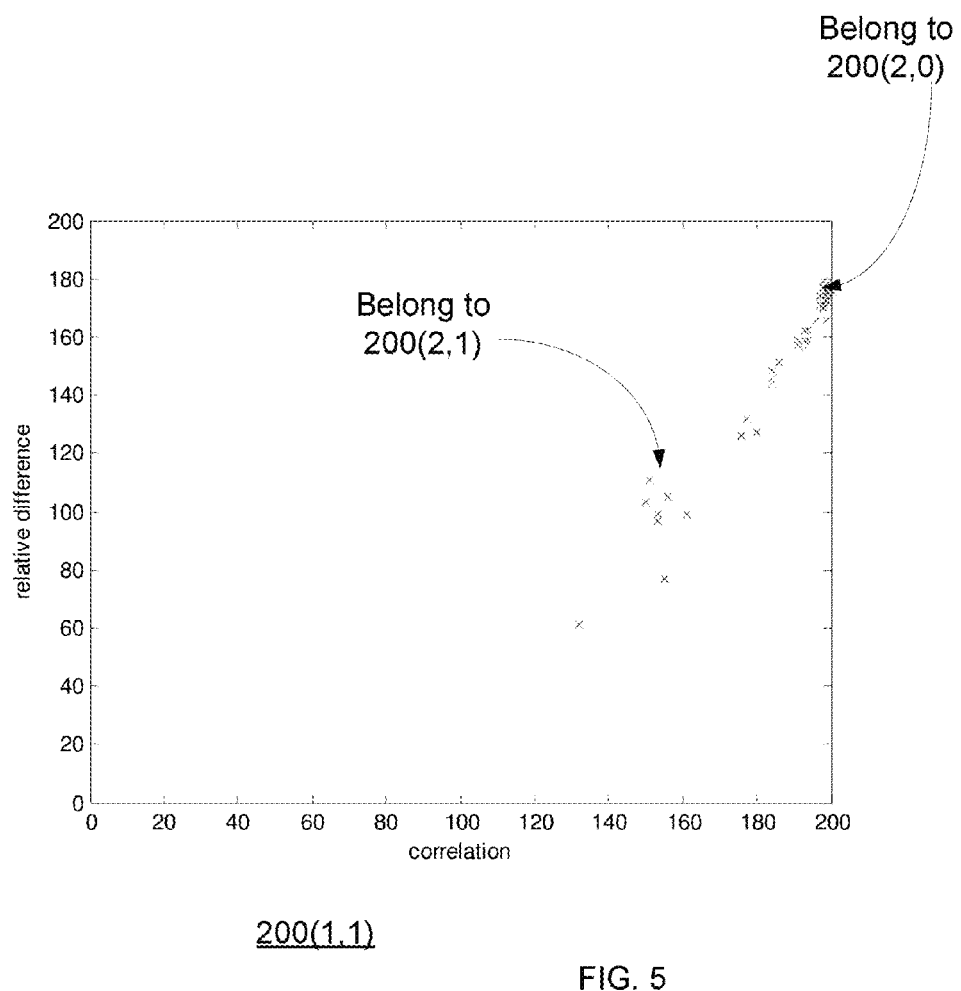
FIG. 5 illustrates attributes of QRS complex vectors that belong to a node of the cluster tree that is about to be split to two nodes according to an embodiment of the invention.
Figure 6:
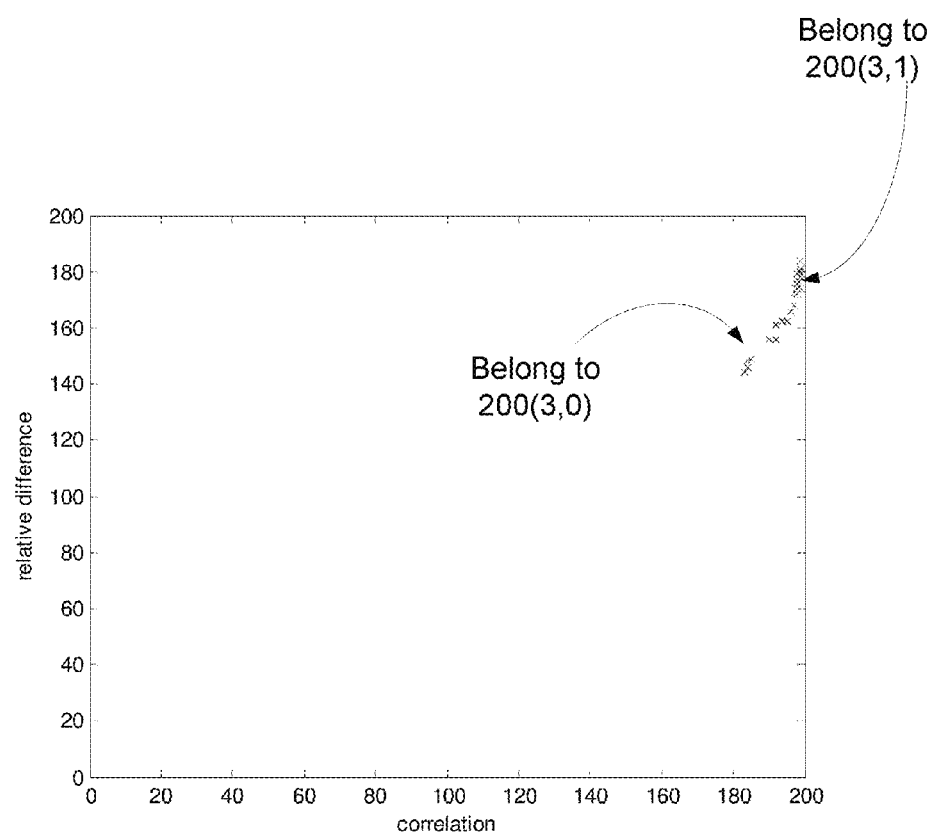
FIG. 6 illustrates attributes of QRS complex vectors that belong to a node of the cluster tree that is about to be split to two nodes according to an embodiment of the invention.
Figure 7:
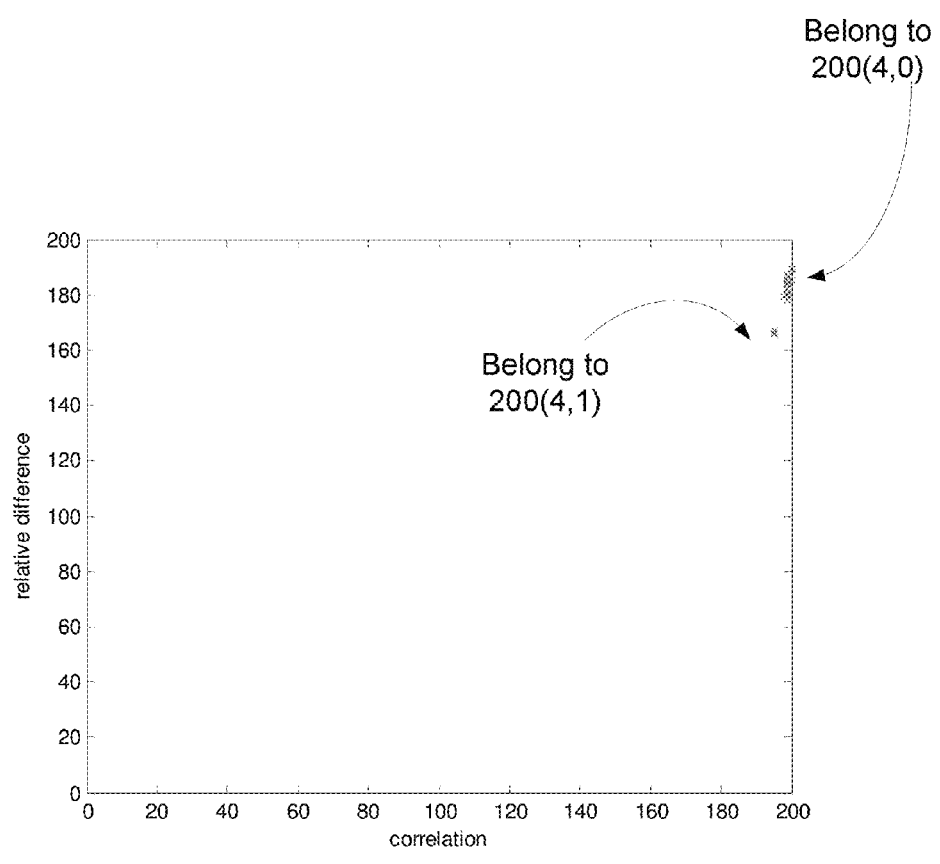
FIG. 7 illustrates attributes of QRS complex vectors that belong to a node of the cluster tree that is about to be split to two nodes according to an embodiment of the invention.

FIG. 3 illustrates a binary tree that includes nine nodes 200(0,0)-200(4,0) out of which nodes 200(1,0), 200(2,1), 200(3,1), 200(4,1) and 200(4,0) are leaf nodes. Node 200(0, 0) is the root node. The childes of node 200(0,0) are nodes 200(1,1) and 200(1,0). The childes of node 200(1,1) are nodes 200(2,1) and 200(2,0). The childes of node 200(2,0) are nodes 200(3,1) and 200(3,0). The childes of node 200(3,0) are nodes 200(4,1) and 200(4,0).

Nodes 200(0,0)-200(4,0) include:

a. QRS complex data 203(0,0)-203(4,0) that provides information about the QRS complex vectors that belong to the node. This information may include the QRS complex vectors themselves, attributes and/or parameters of the QRS complexes themselves and the like.

b. QRS complex templates 202(0,0)-202(4,0).

FIG. 3 also shows the number of QRS complexes that belong to each node—these numbers are referred to as 202(0,0)-202(4,0). Thus, nodes 200(0,0)-200(4,0) include 128, 48, 80, 21, 27, 7, 20, 2 and 18 QRS complexes respectively.

FIG. 3-7 illustrates attributes of QRS complexes that belong to nodes 200(0,0), 200(1,1), 200(2,0) and 200(3,0) respectively.

These figures illustrate that:

a. Node 200(0,0) includes attributes of QRS complexes that are relative to its QRS complex template 202(0,0) and are split to nodes 200(1,1) and 200(1,0).

b. Node 200(1,1) includes attributes of QRS complexes that are relative to its QRS complex template 202(1,1) and are split to nodes 200(2,1) and 200(2,0).

c. Node 200(2,0) includes attributes of QRS complexes that are relative to its QRS complex template 202(2,0) and are split to nodes 200(3,1) and 200(3,0).

d. Node 200(3,0) includes attributes of QRS complexes that are relative to its QRS complex template 202(3,0) and are split to nodes 200(4,1) and 200(4,0).

The binary tree can be calculated by:

a. Calculating a QRS complex template T for the root node.
b. Calculating, for each QRS complex vector Xi the two following features:
   i. Normalized correlation—$C(T, x_i)$,
   ii. Relative absolute difference—$D(T, x_i)$.
c. Performing K-means clustering on the features space of the tree node.
d. Calculating a criterion based on Mahalanobis distance of the feature space data points.
e. Splitting the node if two or more models are found according to the criterion.

The binary tree can be then further processed by merging nodes and/or pruning nodes.

The merging may be executed in an iterative manner and may include:

a. Calculating the leaves cross-grade matrix $$\left(1 + \frac{C(L_i, L_j)}{2}\right) \cdot D(L_i, L_j).$$

b. Merging each couple of leaves having a cross-grade higher than pre-defined threshold.
c. Merging the secondary leaf (having less QRS complexes data) to the route from the main leaf to their youngest common ancestor (i.e. all the main leaf ancestors which are not ancestors to the secondary leaf).
d. Subtracting the secondary leaf from the route to their youngest common ancestor (i.e. all the secondary leaf ancestors which are not ancestors to the main leaf).

Figure 8:
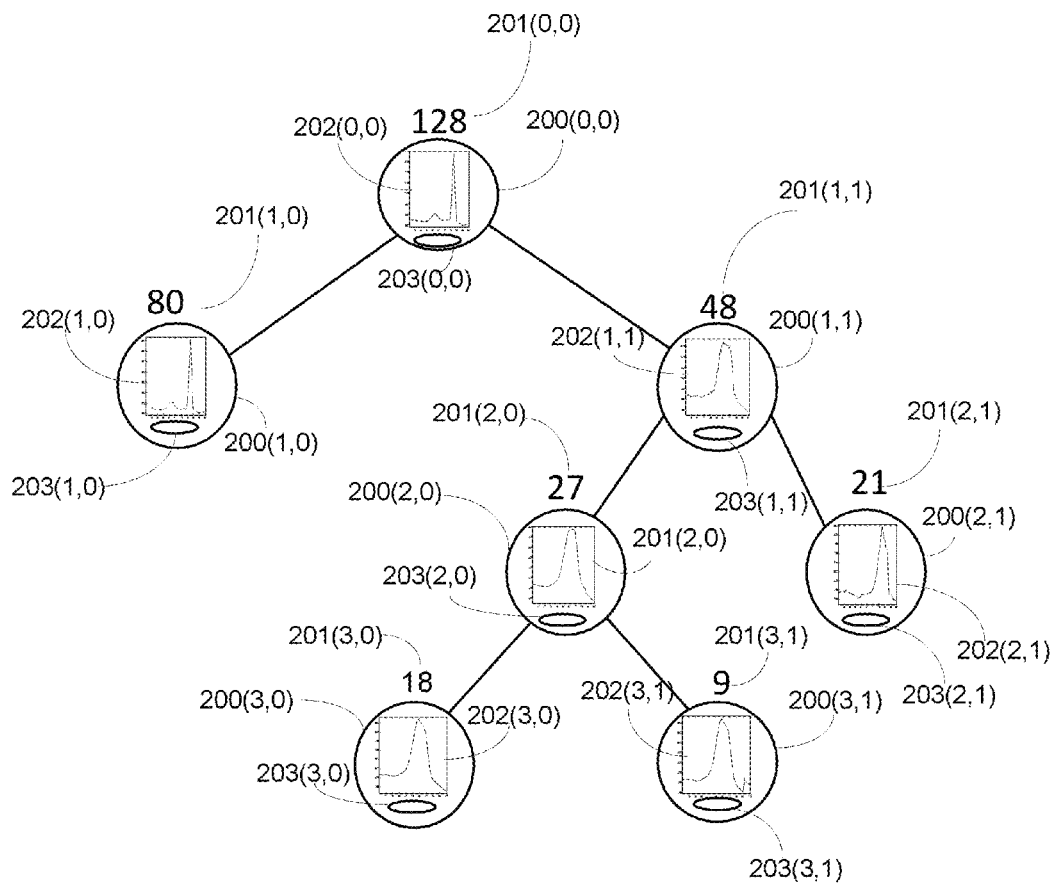
FIG. 8 illustrates a cluster tree according to an embodiment of the invention.

For example:

a. Stage (b) may include merging leaf 200(4, 1) of FIG. 3 is merged with leaf 200(3, 1) of FIG. 3. Thus—the QRS complexes previously represented by leaf 200(4, 1) are added to the QRS complexes of leaf 200(3, 1). Then, leaf 200(4, 0) will replace their father node 200(3, 0).

b. Stage (c) is skipped since all the ancestors of 200(3, 1) are also of 200(4, 1).

c. Stage (d) is skipped since the only ancestor 200(4, 1) has been already updated in stage (b) when being replaced by 200(4, 0).

d. Providing initialized binary tree 200' of FIG. 8.

FIG. 1 illustrates method 10 according to an embodiment of the invention.

Method 10 starts by stage 20 of obtaining a QRS complex vector for each QRS complex of the patient. Each QRS complex vector includes samples of the QRS complex.

The QRS complex vectors can be obtained from one or more leads.

Stage 20 may be followed by stage 30 of calculating a QRS complex template T.

Stage 30 may include stage 32 of calculating the weighted mean QRS complex vector.

Figure 10:
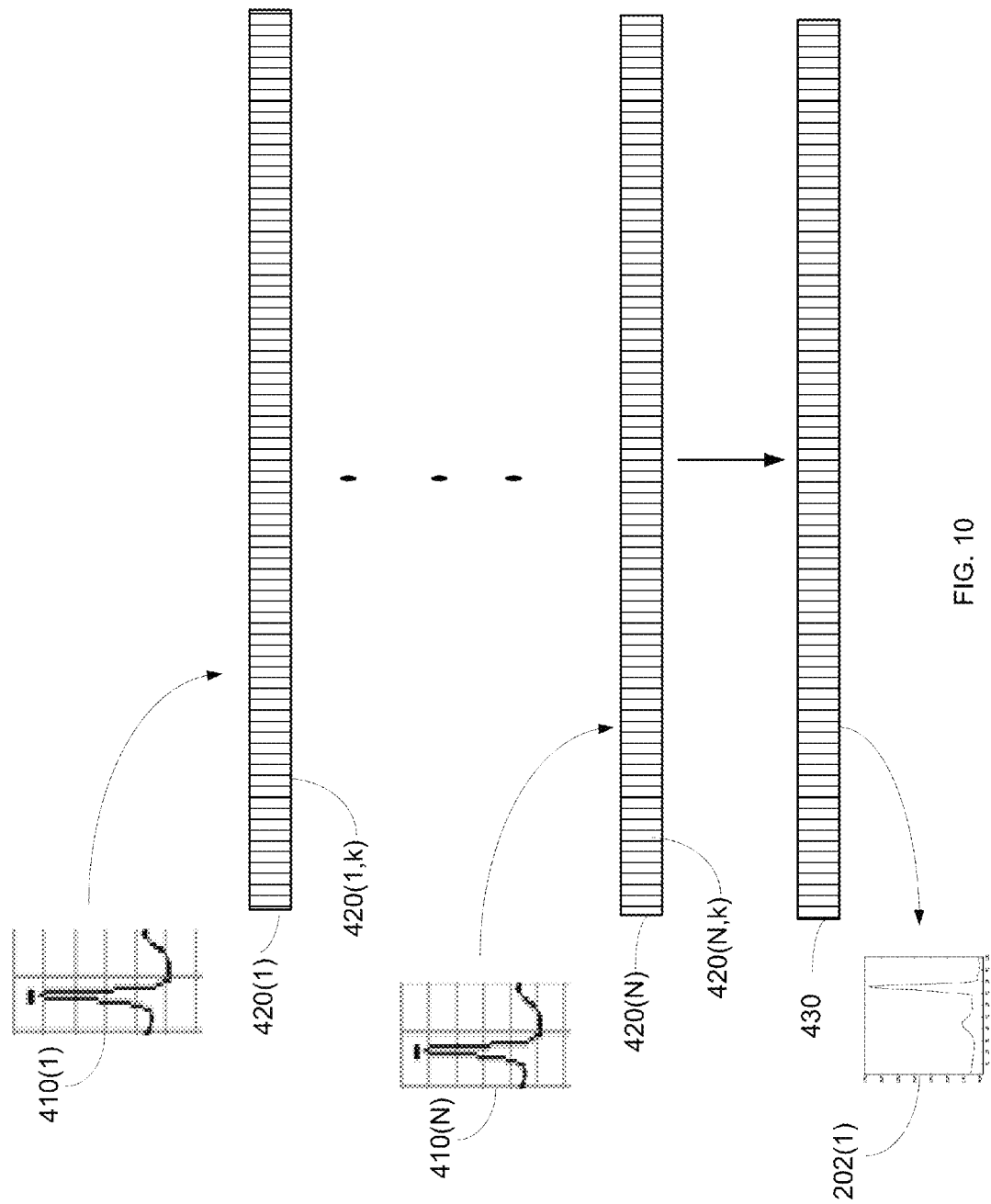
FIG. 10 illustrates QRS complexes, QRS complex vectors representative of the QRS complexes and a QRS complex template according to an embodiment of the invention.

FIG. 10 illustrates multiple (N) QRS complexes 410(1)-410(N) that are represented by N QRS complex vectors 420(1)-420(N), each QRS complex includes multiple elements (that represents samples) such as 420(1,k) and 420(N,m). Assuming that all these QRS complex vectors belong to the same cluster they are represented by QRS complex template 430. The QRS complex template 430 may represent a synthetic QRS complex 202(1).

Referring back to FIG. 1—stage 30 may include stage 34 of calculating a template QRS complex vector that is not the weighted mean QRS vector. This occurs when the weighted mean QRS vector has balanced weighting of clusters and therefore does not represent any cluster.

The template QRS complex vector (that is not the weighted mean QRS vector) may be a median vector of all QRS complex vectors (stage 36) or may be a template QRS vector that differs from the weighted mean QRS vector and from the median vector (stage 38).

For example—when the median vector is not homogeneous (not represents the same cluster in each sample of the vector) the closest QRS complex to the median vector by the criterion of relative absolute distance—$D(\vec{X}_i, \vec{T})$ is chosen to be the template.

Stage 30 may be followed by stage 40 of calculating, for each QRS complex vector Xi, QRS complex vector attributes that represent the relationship between the QRS complex vector and the QRS complex template complex vector T.

Stage 40 may include stage 42 of calculating $$D(\vec{X}_i, \vec{T}) = 1 - \frac{S_A(\vec{X}_i - \vec{T})}{S_A(\vec{X}_i) + S_A(\vec{T})}$$

where $S(\vec{v}) = \sum_{k=1}^{N} |\vec{v}[k]|$ is the sum of absolute values of vector $\vec{v}$.

Stage 40 may include stage 44 of calculating $C(\vec{X}_i, \vec{T})$ where $$C(\vec{X}_i, \vec{T}) = \frac{1}{2} \cdot \left(1 + \frac{\text{cov}(\vec{X}_i, \vec{T})}{\sigma_{X_i} \cdot \sigma_T}\right).$$

Stage 40 may be followed by stage 50 of calculating clusters based upon the QRS complex attributes to provide a cluster tree, clusters are mapped to cluster tree nodes. The clusters are calculated within a two dimensional attribute (C, D) space.

Stage 50 may include stage 52 of performing K-means clustering—assuming that K different reference points belong to different clusters and then starting associate attributes of QRS complex vectors to these clusters.

Stage 50 may include stage 54 of performing clustering that differ from K-means clustering.

Stage 50 may include stage 56 of splitting nodes.

Stage 56 may include stage 562 of:
a. Assuming that a node includes two potential clusters (primary—higher attributes score and secondary—lower attributes score).
b. Calculating the minimal Mahalanobis distance of a point from the secondary potential cluster to the primary potential cluster.
c. Calculating the maximal Mahalanobis distance of a point of the primary potential cluster to the primary potential cluster.
d. Splitting if a ratio between the minimal and maximal Mahalanobis distances fulfills a criterion (for example—exceeds a threshold such as but not limited to 2.5).

Stage 56 may include stage 564 of performing other splitting decision criterion such as using SVM algorithm.

Stage 50 may include stage 58 of merging leaf nodes.

Stage 58 may include stage 582 of calculating leaves cross-grades, merge leaves (primary & secondary) having a cross-grade higher than threshold, merge the secondary leaf data to all non-common ancestors of the primary leaf (primary route) and subtract its data from all his all non-common ancestors (secondary route).

Stage 50 may include stage 59 of pruning the cluster tree.

Stage 50 may be followed by stage 60 of labeling clusters.

Stage 60 may take into account information about QRS complexes of the patient and also may take into account information about QRS complexes of other people—about the entire population, about a subset of the population and the like.

The labeling may include determining, for each leaf, the likelihood that is belongs to a certain type of cluster—for example, normal, PAC or PVC type and applying a maximum likelihood criterion to find the appropriate type.

Each type of leaf has a template that has parameters. For each leaf and for each type of potential label calculating a sum of the following parameters:
$L_w$—likelihood of QRS template width for each type of leaf
$L_{rw}$—likelihood of QRS template relative width to biggest leaf
$L_{rr}$—likelihood of QRS template RR ratio for each type of leaf
$L_e$—likelihood of energy of normalized QRS template for each type of leaf
$L_c$—likelihood of QRS template correlation to biggest leaf
$L_p$—likelihood of P wave existence in QRS template for each type of leaf Selecting, for each leaf, the type that is associated with the biggest sum (Related to the leaf).

The labeling may be executed after the initialization phase, whenever an unclassified leaf contain a certain number (for example five or more) QRS complexes and its feature space is dense enough, or whenever a predefined number (for example 50) of new QRS complexes was added to a leaf.

When the greatest leaf (leaf having the most QRS complexes such as leaf 200(3) of FIG. 3) is changed, re-labeling of all labeled leaves may be needed.

Update Phase

The update phase may include finding to each new QRS complex the best matching cluster and label it.

The finding of the best matching leaf for new QRS can include calculating for each leaf the Euclidean distance between its grades vector to all the tree leaves and the grades vector of the new QRS to all other leaves: $D_G(x, l_i) = \sqrt{\sum_{j=1}^{|L|} \{G(x,l_j) - G(l_i,l_j)\}^2}$ and selecting the leaf with the minimal distance as the best matching leaf.

Function $G(\vec{A}, \vec{B})$ is the similarity grade between the vectors $\vec{A}$ and $\underline{B}$, where $$G(\vec{A}, \vec{B}) = \left(1 + \frac{C(\vec{A}, \vec{B})}{2}\right) \cdot D(\vec{A}, \vec{B}).$$

$\vec{A}$ and $\vec{B}$ can represent a QRS complex vector or a QRS complex template.

Figure 9:
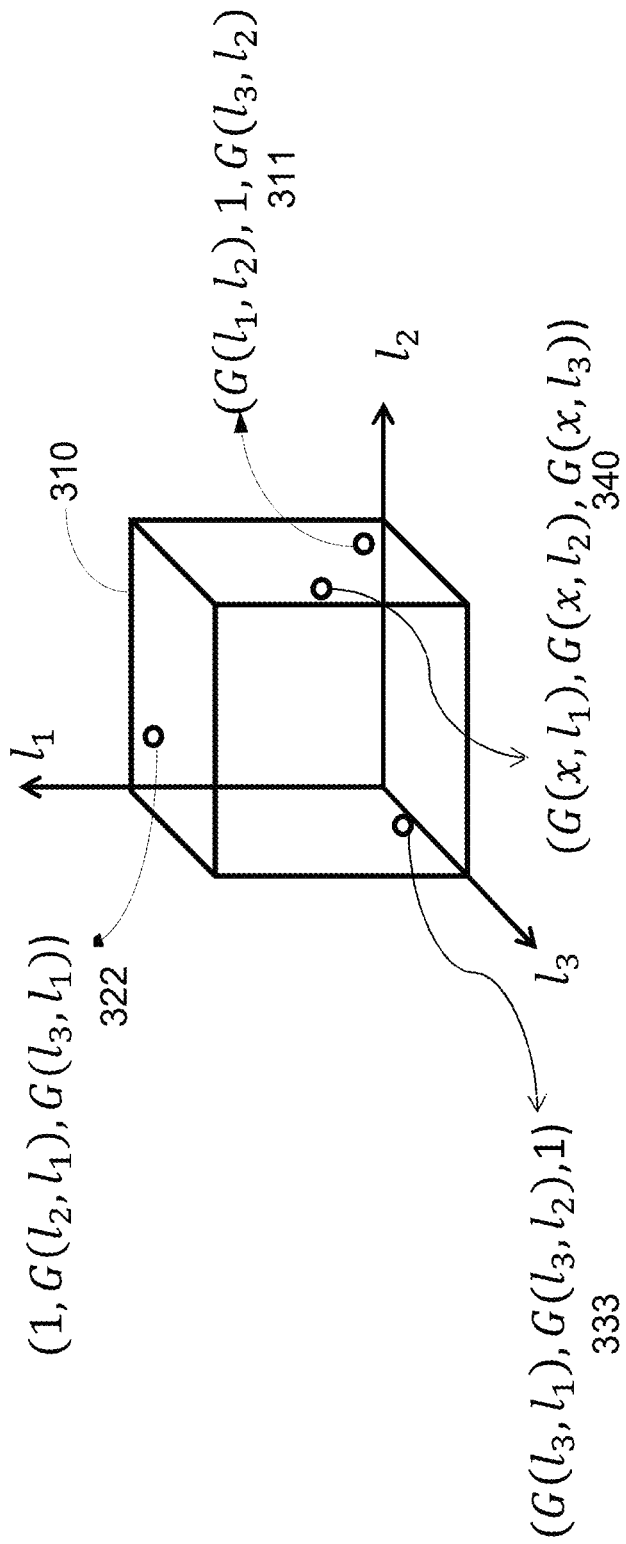
FIG. 9 illustrates a three dimensional space representative of distances to three leaves of a binary tree that has three leaves according to an embodiment of the invention.

The matching can be executed within a multi-dimensional space having L dimensions, L being the number of leaves of the binary tree. FIG. 9 illustrates a three-dimensional space 310 (L=3) in which similarity values to each one of the three leaves (l1, l2 and l3) are calculated.

In FIG. 9 there are shown three template points 311, 322 and 322 that represent the similarity vectors to leaf l1 (311), l2 (322) and l3 (333). The new QRS complex is represented by similarity vector 340 that represents the similarity of the new QRS complex $\vec{X}$ to the three leaves.

For each dimension of the multi-dimensional space a similarity value is calculated by applying function $$G(\vec{A}, \vec{B}) = \left(1 + \frac{C(\vec{A}, \vec{B})}{2}\right) \cdot D(\vec{A}, \vec{B})$$

The best matching leaf can be found in other manners. For example, if the new QRS complex does not sufficiently match the best matching leaf. This may include finding the best matching QRS complex based upon a match between QRS complex parameter such as RR or RR ratio (RR ratio is the ratio between (a) the time difference between the current QRS complex and a previous QRS complex, and (b) the time difference between the current QRS complex and the next detected QRS complex.

After the best matching leaf is found the binary tree can be updated—split, merged and/or undergo a pruning process.

The best matching leaf can be analyzed to determine whether it should be split. If it is split and two new leafs are created, the binary tree should undergo a merge process. The labeling of the tree and especially a labeling of a newly formed leaf can be done whenever a split or merge is performed. A newly formed leaf can also be pruned.

The pruning can be done, for example, after splitting a node, the right new leaf which contains the secondary cluster, is checked for pruning or when an unclassified leaf is updated.

A leaf can be pruned if the leaf is unclassified, the leaf contains more than pre-defined amount of QRS complexes and the leaf's features space is dispersed.

FIG. 2 illustrates method 100 according to an embodiment of the invention.

Method 100 starts by stage 110 of receiving new QRS complex vector.

Stage 110 may be followed by stage 120 of finding a best matching cluster (leaf).

Stage 120 may include stage 122 of finding best matching cluster by finding the cluster with the QRS complex template attributes that are closets to the attributes of the new QRS complex.

Stage 120 may include stage 124 of finding best matching cluster by comparing new QRS complex parameters (such as RR and RR ratio) to QRS complex template equivalent parameters.

Stage 120 may be followed by stage 130 of adding new QRS complex vector to the best matching cluster and updating cluster statistical data.

Stage 130 may be followed by stage 140 of updating the cluster tree.

Stage 140 may be followed by stage 150 of splitting the updated cluster

Stage 150 may be followed by stage 160 of merging the some leaves in the cluster tree Stage 160 may be followed by stage 170 of pruning the updated leaf Stage 170 may be followed by stage 180 of labeling the updated leaf or a merged leaf.

Method 100 may be executed for multiple newly received QRS complexes—from one or more leads. It is noted that QRS complexes detected from different leads can be equally treated or can be assigned different weight—based upon expected (or measured) reliability of the leads. If, for example, a first lead is more reliable (less noisy) than a second lead, the QRS complexes obtained from the first lead can receive more weight.

In case of multiple leads the following calculations can be made:

For each QRS complex vector i (or a QRS template vector) at lead j-$X_j[i]$ calculate:

a. Calculate the normalized vector $\tilde{X}_j[i]$ to have a peak-to-peak value of 1 and its baseline is zero.

b. Calculate $E(\tilde{X}_j[i])$—the energy of the normalized vector c. Calculate $E_d(\tilde{X}_j[i])$—the energy of the normalized vector derivative.

d. Calculate the QRS complex vector weight $$W(X_j[i]) = \frac{1}{\sqrt{E(\tilde{X}_j[i])^2 + E_d(\tilde{X}_j[i])^2}}$$

Every attribute A of a QRS complex (such as C(X[i], T), D(X[i], T), width, energy, etc.) will be calculated as the weighted mean of the QRS per leads attributes as follow:

$$A(X[i]) = \sum_{j=1}^{N} W(X_j[i]) \cdot A(X_j[i])$$

The multi-lead similarity grade between two QRS templates vectors will be calculated as follow:

$$W_j(T_k, T_l) = \frac{W_j(T_k) \cdot N_k + W_j(T_l) \cdot N_l}{N_k + N_l},$$

where $N_k$ is the number of QRSs in leaf k.

$$G(T_k, T_l) = \sum_{j=1}^{N} W_j(T_k, T_l) \cdot G_j(T_k, T_l)$$

Figure 11:
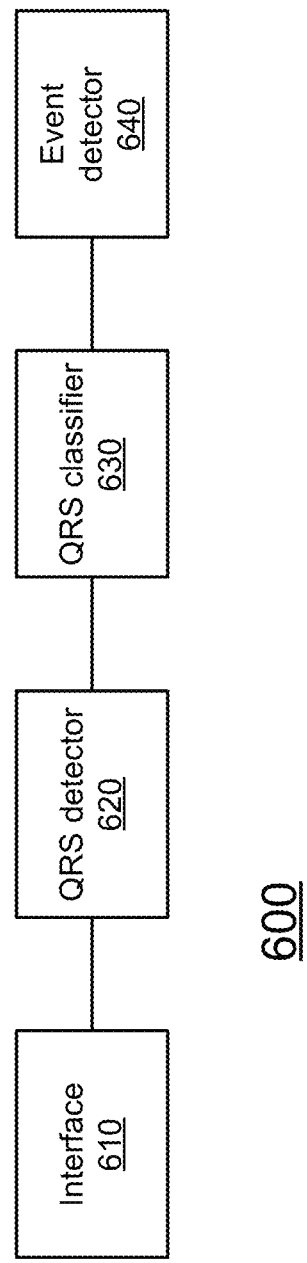
FIG. 11 illustrates a system according to an embodiment of the invention.

FIG. 11 illustrates system 600 according to an embodiment of the invention. The system 600 includes hardware components and circuits. The hardware components may execute instructions embedded in non-transitory computer readable media such as memory modules of any kind. System 600 can be a computer or a hardware processor.

System 600 includes interface 610 for receiving electrocardiograph signals. These signals can be provided from electrodes, sensor front ends, leads and the like. The electrocardiograph signals may be analog or digital signals. If analog—the interface 610 or the QRS detector 620 may samples these analog signals to provide digital electrocardiograph signals.

The interface 610 is followed by the QRS detector 620 that detects QRS complexes and outputs observations of the QRS complexes to the QRS classifier 630. The observations may be QRS complex vectors that include multiple elements and/or other features extracted from those vectors.

The QRS classifier 630 may execute method 10 and 100 or a combination thereof. After being initialized it classified each new QRS complex and may send an indication about the class (label) of the new QRS complex.

The event detector 640 may process the indications sent by the QRS classifier to detect medical events such as disorders in the heart functions. The event detector 640 can sent alerts to other systems.

The invention may also be implemented in a computer program for running on a computer system, at least including code portions for performing steps of a method according to the invention when run on a programmable apparatus, such as a computer system or enabling a programmable apparatus to perform functions of a device or system according to the invention. The computer program may cause the storage system to allocate disk drives to disk drive groups.

A computer program is a list of instructions such as a particular application program and/or an operating system. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system.

The computer program may be stored internally on a non-transitory computer readable medium. All or some of the computer program may be provided on computer readable media permanently, removably or remotely coupled to an information processing system. The computer readable media may include, for example and without limitation, any number of the following: magnetic storage media including disk and tape storage media; optical storage media such as compact disk media (e.g., CD ROM, CD R, etc.) and digital video disk storage media; nonvolatile memory storage media including semiconductor-based memory units such as FLASH memory, EEPROM, EPROM, ROM; ferromagnetic digital memories; MRAM; volatile storage media including registers, buffers or caches, main memory, RAM, etc.

A computer process typically includes an executing (running) program or portion of a program, current program values and state information, and the resources used by the operating system to manage the execution of the process. An operating system (OS) is the software that manages the sharing of the resources of a computer and provides programmers with an interface used to access those resources. An operating system processes system data and user input, and responds by allocating and managing tasks and internal system resources as a service to users and programs of the system.

The computer system may for instance include at least one processing unit, associated memory and a number of input/output (I/O) devices. When executing the computer program, the computer system processes information according to the computer program and produces resultant output information via I/O devices.

In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

The connections as discussed herein may be any type of connection suitable to transfer signals from or to the respective nodes, units or devices, for example via intermediate devices. Accordingly, unless implied or stated otherwise, the connections may for example be direct connections or indirect connections. The connections may be illustrated or described in reference to being a single connection, a plurality of connections, unidirectional connections, or bidirectional connections. However, different embodiments may vary the implementation of the connections. For example, separate unidirectional connections may be used rather than bidirectional connections and vice versa. Also, plurality of connections may be replaced with a single connection that transfers multiple signals serially or in a time multiplexed manner. Likewise, single connections carrying multiple signals may be separated out into various different connections carrying subsets of these signals. Therefore, many options exist for transferring signals.

Although specific conductivity types or polarity of potentials have been described in the examples, it will be appreciated that conductivity types and polarities of potentials may be reversed.

Each signal described herein may be designed as positive or negative logic. In the case of a negative logic signal, the signal is active low where the logically true state corresponds to a logic level zero. In the case of a positive logic signal, the signal is active high where the logically true state corresponds to a logic level one. Note that any of the signals described herein may be designed as either negative or positive logic signals. Therefore, in alternate embodiments, those signals described as positive logic signals may be implemented as negative logic signals, and those signals described as negative logic signals may be implemented as positive logic signal.

Furthermore, the terms "assert" or "set" and "negate" (or "deassert" or "clear") are used herein when referring to the rendering of a signal, status bit, or similar apparatus into its logically true or logically false state, respectively. If the logically true state is a logic level one, the logically false state is a logic level zero. And if the logically true state is a logic level zero, the logically false state is a logic level one.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures may be implemented which achieve the same functionality.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected," or "operably coupled," to each other to achieve the desired functionality Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner.

Also for example, the examples, or portions thereof, may implemented as soft or code representations of physical circuitry or of logical representations convertible into physical circuitry, such as in a hardware description language of any appropriate type.

Also, the invention is not limited to physical devices or units implemented in non-programmable hardware but can also be applied in programmable devices or units able to perform the desired device functions by operating in accordance with suitable program code, such as mainframes, minicomputers, servers, workstations, personal computers, notepads, personal digital assistants, electronic games, automotive and other embedded systems, cell phones and various other wireless devices, commonly denoted in this application as 'computer systems.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

I claim:

1. A method for QRS classification, the method comprises:
generating, by a computer and based upon information representative of multiple QRS complexes of a patient, a QRS complex cluster tree;
wherein the generating of the QRS complex cluster tree comprises calculating, for each QRS complex cluster, a QRS complex template based upon the information representative of multiple QRS complexes of a patient to provide QRS complex clusters; and clustering based upon statistical attributes to the QRS complex template;
wherein a QRS complex template of a QRS complex cluster is selected out of (a) a weighted mean of QRS complex vectors that belong to the QRS complex cluster; and (b) a median of QRS complex vectors that belong to the QRS complex cluster;
updating, by the computer, the QRS complex cluster tree based upon information relating to other QRS complexes of the patient; wherein the updating of the QRS complex cluster tree comprises receiving another QRS complex of the patient; and classifying the other QRS complex thereby finding a best matching cluster; and
sending an alert about a medical event of which the other QRS complex is indicative of.

2. The method according to claim 1 wherein the generating of the QRS complex cluster tree comprises:
associating different QRS complex clusters to different leaves of the QRS complex cluster tree.

3. The method according to claim 2 wherein the calculating of the QRS complex clusters is based solely on the information representative of the multiple QRS complexes of the patient.

4. The method according to claim 3 comprising labeling the QRS complex clusters based upon (a) the information representative of the multiple QRS complexes of the patient, and (b) information representative of QRS complexes of at least one other person.

5. The method according to claim 1 wherein the QRS complex template of the QRS complex cluster is the weighted mean of QRS complex vectors that belong to the QRS complex cluster.

6. The method according to claim 1 wherein the QRS complex template of the QRS complex cluster is the median of QRS complex vectors that belong to the QRS complex cluster.

7. The method according to claim 1 wherein the medical event is a disorder in a heart function.

8. The method according to claim 1 wherein the information representative of multiple QRS complexes of a patient is obtained from a single lead.

9. The method according to claim 1 wherein the information representative of multiple QRS complexes of a patient is obtained from multiple leads.

10. A non-transitory computer readable medium that stores instructions that once executed by the computer cause the computer to execute the stage of:
generating, based upon information representative of multiple QRS complexes of a patient, a QRS complex cluster tree;
wherein the generating of the QRS complex cluster tree comprises calculating, for each QRS complex cluster, a QRS complex template based upon the information representative of multiple QRS complexes of a patient to provide QRS complex clusters; and clustering based upon statistical attributes to the QRS complex template;
wherein a QRS complex template of a QRS complex cluster is selected out of (a) a weighted mean of QRS complex vectors that belong to the QRS complex cluster; and (b) a median of QRS complex vectors that belong to the QRS complex cluster;
updating the QRS complex cluster tree based upon information relating to other QRS complexes of the patient; wherein the updating of the QRS complex cluster tree comprises receiving another QRS complex of the patient; and classifying the other QRS complex thereby finding a best matching cluster; and
sending an alert about a medical event of which the other QRS complex is indicative of.

11. The non-transitory computer readable medium according to claim 10 that stores instructions for associating different QRS complex clusters to different leaves of the QRS complex cluster tree.

12. The non-transitory computer readable medium according to claim 11 that stores instructions for calculating of the QRS complex clusters based solely on the information representative of the multiple QRS complexes of the patient.

13. The non-transitory computer readable medium according to claim 12 that stores instructions for labeling the QRS complex clusters based upon (a) the information representative of the multiple QRS complexes of the patient, and (b) information representative of QRS complexes of at least one other person.

14. The non-transitory computer readable medium according to claim 10 wherein the QRS complex template of the QRS complex cluster is the weighted mean of QRS complex vectors that belong to the QRS complex cluster.

15. The non-transitory computer readable medium according to claim 10 wherein the QRS complex template of the QRS complex cluster is the median of QRS complex vectors that belong to the QRS complex cluster.

16. The non-transitory computer readable medium according to claim 10 wherein the medical event is a disorder in a heart function.

17. The non-transitory computer readable medium according to claim 10 wherein the information representative of multiple QRS complexes of a patient is obtained from a single lead.

18. The non-transitory computer readable medium according to claim 10 wherein the information representative of multiple QRS complexes of a patient is obtained from multiple leads.

19. A system for QRS classification, the system comprises a computer that comprises an event detector and a QRS classifier;
   wherein the QRS classifier is arranged to:
   generate, based upon information representative of multiple QRS complexes of a patient, a QRS complex cluster tree;
   wherein a generating of the QRS complex cluster tree comprises calculating, for each QRS complex cluster, a QRS complex template based upon the information representative of multiple QRS complexes of a patient to provide QRS complex clusters; and clustering based upon statistical attributes to the QRS complex template;
   wherein a QRS complex template of a QRS complex cluster is selected out of (a) a weighted mean of QRS complex vectors that belong to the QRS complex cluster; and (b) a median of QRS complex vectors that belong to the QRS complex cluster;
   update the QRS complex cluster tree based upon information relating to other QRS complexes of the patient; wherein the updating of the QRS complex cluster tree comprises receiving another QRS complex of the patient; and classifying the other QRS complex thereby finding a best matching cluster; and
   wherein the event detector is arranged to send an alert about a medical event of which the other QRS complex is indicative of.

20. The system according to claim 19 wherein the QRS classifier is arranged to associate different QRS complex clusters to different leaves of the QRS complex cluster tree.

21. The system according to claim 20 wherein the QRS classifier is arranged to calculate the QRS complex clusters solely on the information representative of the multiple QRS complexes of the patient.

22. The system according to claim 20 wherein the medical event is a disorder in a heart function.

23. The system according to claim 19 wherein the QRS classifier is arranged to calculate the QRS complex template of the QRS complex cluster as the weighted mean of QRS complex vectors that belong to the QRS complex cluster.

24. The system according to claim 19 wherein the QRS classifier is arranged to calculate the QRS complex template of the QRS complex cluster as the median of QRS complex vectors that belong to the QRS complex cluster.

25. The system according to claim 19 wherein the information representative of multiple QRS complexes of a patient is obtained from a single lead.

26. The system according to claim 19 wherein the information representative of multiple QRS complexes of a patient is obtained from multiple leads.

* * * * *